United States Patent [19]

Houston et al.

[11] Patent Number: 5,318,790
[45] Date of Patent: Jun. 7, 1994

[54] POLYOL POLYESTER PURIFICATION

[75] Inventors: Robert Houston, Cincinnati; Robert J. Sarama, Loveland; Paul Seiden, Cincinnati; Keith D. Adams, Cincinnati; Gregory M. McCabe, Cincinnati, all of Ohio

[73] Assignee: The Procter & Gamble Company, Cincinnati, Ohio

[21] Appl. No.: 872,227

[22] Filed: Apr. 22, 1992

Related U.S. Application Data

[63] Continuation-in-part of Ser. No. 590,022, Oct. 2, 1990, abandoned, which is a continuation-in-part of Ser. No. 422,279, Oct. 16, 1989, abandoned.

[51] Int. Cl.$^5$ .................................................. A23L 1/015
[52] U.S. Cl. ...................................... 426/423; 426/330; 426/442; 426/611; 536/119; 536/124; 502/407
[58] Field of Search .......... 426/601, 611, 330, 330.6, 426/423, 442; 260/410.6; 536/119, 124

[56] References Cited

U.S. PATENT DOCUMENTS

| | | | |
|---|---|---|---|
| 3,600,186 | 8/1971 | Mattson | 426/611 |
| 3,963,699 | 6/1976 | Rizzi et al. | 260/234 |
| 4,517,360 | 5/1985 | Volpenhein | 536/119 |
| 4,518,772 | 5/1985 | Volpenheim | 536/119 |
| 4,565,794 | 1/1986 | de Buda | 502/83 |
| 4,629,588 | 12/1986 | Welsh et al. | 260/428 |
| 4,954,621 | 9/1990 | Masaoka et al. | 536/119 |
| 5,124,301 | 6/1992 | Wyness et al. | 502/171 |

FOREIGN PATENT DOCUMENTS

| | | | |
|---|---|---|---|
| 108571 | 5/1984 | European Pat. Off. | C11B 3/10 |
| 424066 | 4/1991 | European Pat. Off. | C07H 13/06 |

OTHER PUBLICATIONS

Anderson, A. J. C., 1962, "Refining Oils & Fats for Edible Purposes", 2nd Ed., Pergaman Press, Oxford, UK, pp. 148-149.
The Procter & Gamble Company, "Olestra Food Additive Petition", Apr. 1, 1987, pp. 1, 3, 22-23.

*Primary Examiner*—Carolyn Paden
*Attorney, Agent, or Firm*—T. M. Rosnell; G. W. Allen

[57] ABSTRACT

Polyol polyesters are purified by a process comprising bleaching with a specific silica gel and/or heat treatment and removal of volatile products by steam deodorization. Any steam deodorization is at reduced temperatures or in admixture with triglycerides to minimize thermal degradation of the polyol polyesters.

13 Claims, No Drawings

POLYOL POLYESTER PURIFICATION

CROSS-REFERENCE TO RELATED APPLICATION

This is a continuation-in-part of patent application U.S. Ser. No. 07/590,022, filed Oct. 2, 1990, now abandoned which is a continuation-in-part of patent application U.S. Ser. No. 07/422,279, filed Oct. 16, 1989, now abandoned.

TECHNICAL FIELD

This invention relates to improved purification of higher polyol fatty acid polyesters, especially sucrose polyesters, prepared via transesterification, and more specifically to removal of undesirable reaction products like color materials and polar components from said fatty acid polyesters and to inhibition or prevention of the formation of free fatty acids and dimer methyl esters.

BACKGROUND OF THE INVENTION

Processes for preparing polyol fatty acid polyesters, including solvent-free transesterification reactions, have been described in U.S. Pat. No. 3,963,699, Rizzi et al., issued Jun. 15, 1976; U.S. Pat. No. 4,517,360, Volpenhein, issued May 14, 1985; and U.S. Pat. No. 4,518,772, Volpenhein, issued May 21, 1985; all of said patents being incorporated herein by reference.

In order to have a better commercial process it is desirable to have available a number of improvements, e.g., purification procedures that can better remove undesirable color materials from the polyol fatty acid polyesters. Each of said improvements individually can improve the finished product and the combination of the improvements can provide a truly superior product.

SUMMARY OF THE INVENTION

The present invention relates to improved, commercial, processes for removing minor amounts of undesirable materials such as color materials; materials that affect odor or flavor; or precursors of such materials, from higher polyol fatty acid polyesters and for preventing or inhibiting the formation of free fatty acids and dimer methyl esters, which comprise a process step selected from the group consisting of: (1) treating the said polyesters during or following the refining steps with a silica gel having: (a) average particle size of from about 10 to about 30 microns; (b) average pore diameter of from about 50 to about 70 Angstrom Units; (c) surface area of from about 720 to about 800 square meters per gram; (d) pore volume of from about 0.9 to about 1.9 cc/g; (e) PH, measured at a level of about 5% in water, of from about 5 to about 8; and (f) total volatiles of less than about 20%; (2) heat treating the said polyesters to reduce the content of peroxygen groups and removing the resulting undesirable volatile materials by, e.g., steam stripping, preferably either at a temperature below about 450° F. (230° C.) or after first mixing with at least about 25% of a triglyceride to minimize thermal degradation; and (3) removing the undesirable volatile materials, or (4) combinations of steps (1), (2), and (3). The color of the finished product should be lighter than about 1.5, preferably lighter than about 1.2, more preferably lighter than about 0.8 Lovibond Red, and the flavor and odor should be bland. Stability upon exposure to air is increased by up to about a factor of 3 especially when the said silica gel is used to remove undesirable minor components. The purified polyol fatty acid polyester is sufficiently stable that mixtures with at least about 25% of triglyceride containing natural antioxidants are surprisingly stable as compared to mixtures with such triglycerides comprising unpurified polyol fatty acid polyesters.

DETAILED DESCRIPTION OF THE INVENTION

The Polyol Polyesters

As used herein, the term "polyol" is intended to include any aliphatic or aromatic compound containing at least four free hydroxyl groups. In practicing the process disclosed herein, the selection of a suitable polyol is simply a matter of choice. For example, suitable polyols can be selected from the following classes: saturated and unsaturated straight and branched chain linear aliphatics; saturated and unsaturated cyclic aliphatics, including heterocyclic aliphatics; or mononuclear or polynuclear aromatics, including heterocyclic aromatics. Carbohydrates and nontoxic glycols are preferred polyols. Monosaccharides suitable for use herein include, for example, mannose, galactose, arabinose, xylose, ribose, apiose, rhamnose, Psicose, fructose, sorbose, tagitose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol and galactitol. It is desirable that the aldehyde groups be changed to alcohol groups or reacted with alcohol groups to form ether linkages. E.g., the polyol can be an alkyl glycoside or polyglycoside, especially glucosides and polyglucosides.

Particularly preferred classes of materials suitable for use herein include the monosaccharides, the disaccharides and sugar alcohols. Preferred carbohydrates and sugar alcohols include xylitol, sorbitol and sucrose. The most preferred is sucrose.

As used herein, the term "fatty acid esters" is intended to include the $C_1$-$C_4$ (preferably methyl), 2-methoxy ethyl and benzyl esters of fatty acids containing about eight or more carbon atoms, and mixtures of such esters. Suitable reactant esters can be prepared by the reaction of diazoalkanes and fatty acids, or derived by alcoholysis from the fatty acids naturally occurring in fats and oils. Suitable fatty acid esters can be derived from either synthetic or natural, saturated or unsaturated fatty acids and include positional and geometrical isomers. Suitable preferred saturated fatty acids include, for example, caprylic, capric, lauric, myristic, palmitic, stearic, behenic, isomyristic, isomargaric, and anteisoarachadic. Suitable preferred unsaturated fatty acids include, for example, myristoleic, palmitoleic, ricinoleic, linoleic, oleic, elaidic, linolenic, eleostearic, arachidic, arachidonic, erucic, and erythrogenic acids. Mixtures of fatty acids derived from soybean, palm, safflower, rapeseed, canola, peanut, sunflower, cottonseed and/or corn oils are especially preferred for use herein. For example, rapeseed provides a good source for $C_{22}$ fatty acid. $C_{16}$–$C_{18}$ fatty acid can be provided by tallow, soybean oil, or cottonseed oil. Shorter chain fatty acids can be provided by coconut, palm kernel, or babassu oils. Corn oil, lard, olive oil, palm oil, peanut oil, safflower seed oil, sesame seed oil, and sunflower seed oil, are examples of other natural oils which can serve as the source of the fatty acid component.

It is very important for the preparation of improved polyol polyesters that these fatty acid esters be highly purified to remove color/odor materials, oxidation products, and their precursors. Such materials include those that have a color, odor or taste that is objectionable, or which develop an objectionable color, odor, or taste upon heat treatment and/or oxidation. In addition, highly polar materials which coat the catalyst surface should be removed. Preferably, the carbonyl value should be less than about 200 ppm, preferably less than about 100 ppm, more preferably less than about 50 ppm. The percent transmittance at 375 nm with a heptane standard should be greater than zero, preferably greater than 60, most preferably greater than 80. For typical ester sources without added colored materials, these values define operable reactants. I.e., the carbonyl content is generally indicative of the total level of polar materials present. The low level of color/odor materials and/or oxidation products in the reactants helps provide improved color polyol polyester products that can be further improved by a combination of the process improvements set forth herein.

Alkali metal soaps are typically used in the processes for preparing polyol polyesters of the types described herein. As used herein, the term "alkali metal fatty acid soap" is intended to include the alkali metal salts of saturated and unsaturated fatty acids having from about 8 to about 18 carbon atoms. Accordingly, suitable alkali metal fatty acid soaps include, for example, the lithium, sodium, potassium, rubidium, and cesium salts of the fatty acids described hereinbefore, especially saturated fatty acids such as capric, lauric, myristic, palmitic, and stearic acids, as well as mixtures thereof. Palmitic and stearic are preferred. Mixtures of fatty acids derived from soybean oil, palm, peanuts, canola, cottonseed, sunflower oil, safflower oil, and/or corn oil are preferred for use herein. Accordingly, preferred alkali metal fatty acid soaps include, for example, the potassium soap made from soybean oil fatty acids. The essentially fully hydrogenated materials, e.g., I.V. of less than about 8, preferably less than about 2 are especially preferred.

In a preferred process of preparing polyesters of sucrose especially utilizing the methyl esters of soybean oil fatty acids, it is highly desirably to have present an alkali metal, e.g., potassium or sodium, salt of saturated fatty acids containing from about 16 to about 22 carbon atoms. Intimate mixture of the very finely divided ingredients is important to achieving a good reaction.

The basic catalysts generally suitable for use in preparing the polyol polyesters described herein are those selected from the group consisting of alkali metals, such as sodium, lithium and potassium; alloys of two or more alkali metals, such as sodium-lithium and sodium-potassium alloys; alkali metal hydrides, such as sodium, lithium and potassium hydride; and alkali metal alkoxides, such as potassium t-butoxide and sodium methoxide.

In one desirable embodiment of the present invention, the basic catalyst used in the reaction is potassium carbonate, sodium carbonate, barium carbonate, or mixtures of these compounds. It has been found that when these specific compounds are used as the catalyst, increased yields of light colored higher polyol polyesters are obtained when compared to essentially identical reactions carried out using more conventional catalysts, such as sodium hydride, potassium hydride, soap, or sodium methoxide. These preferred catalysts can also be used in admixture with the more conventional basic catalysts, described above. Potassium carbonate is a highly desirable catalyst for use herein. The use of these catalysts is further disclosed and claimed in U.S. Pat. No. 4,517,360, Volpenhein, issued May 14, 1985, entitled "Synthesis of Higher Polyol Fatty Acid Polyesters using Carbonate Catalysts," incorporated herein by reference.

More reactive catalysts such as potassium or sodium methoxide should be protected until their addition into the reaction mixture. Preferably the catalyst should be suspended in, or more preferably encapsulated by, a material that will either be present in the reaction mixture or be readily separated from the reaction mixture. Suitable encapsulating agents include said alkyl esters of, e.g., $C_{16}$–$C_{22}$ fatty acids. Addition of these more alkaline, reactive catalysts in the later stages after the polyol has an average degree of esterification of more than about 60%, preferably more than about 85%, can provide improved reaction kinetics and result in a greater degree of esterification of the polyol yet does not create the level of color/odor materials that would be created if such catalysts are present from the start of the reaction.

The Reaction

In general, by way of example, an initial heterogeneous reaction mixture comprises from about 10% to about 30%, preferably from about 14% to about 18%, by weight of polyol; from about 60% to about 90%, preferably from about 70% to about 80%, by weight of the fatty acid esters; from about 0.1% to about 20%, preferably from about 0.2% to about 10%, by weight of the emulsifier, e.g., alkali metal fatty acid soap; and from about 0.1% to about 3%, preferably from about 0.1% to about 1%, by weight of basic catalyst component. In general it is desirable, and even preferred, to effect the reaction in at least two steps. In any later step, additional fatty acid esters and, optionally, more reactive catalyst are added. In any second, or later step, fatty acid esters are added to raise the overall ratio of fatty acyl groups to the polyol above the theoretical, fully esterified level, e.g., by at least about 25%, or even by at least 50%. The catalyst in the initial step can be potassium carbonate as described hereinbefore or alkali metal hydroxide at a low level and, in any later step, the catalyst can be either the same as the initial catalyst or can also be potassium or sodium methoxide.

The reaction mixture is heated to a temperature within the range from about 240° F. (115° C.) to about 300° F. (150° C.), desirably from about 250° F. (120° C.) to about 280° F. (140° C.), under a pressure of from about 0.1 mm to about 760 mm Hg, and preferably from about 0.3 mm to about 100 mm Hg. It is highly preferred that the reaction mixture, or mixtures, be stirred as vigorously as possible and maintained in as intimate a mixture as is possible.

Finished Product Clean-up

After the reaction has reached the desired state of completion, the catalyst, the excess fatty esters, and the emulsifier, e.g., soap must be destroyed and/or removed if they cannot be used in the eventual consumption of the polyol fatty acid polyesters. The normal materials that are in triglycerides derived from natural sources (naturally occurring triglycerides) are not present in the polyol fatty acid polyesters, since the processing, the reaction, etc. destroy and/or remove such materials. E.g., such normal materials, like phospholipid and tocopherols, are removed in the process for preparing the esters that are reacted with the polyol to form the polyol fatty acid polyesters. The soap and catalyst can be removed to a large extent by a water separation step. Water is added, preferably at a ratio of from about 0.5:1 to about 10:1 relative to the amount of soap being removed. Separation of the soap and catalyst is facilitated by passing the water and reaction-mix through a centrifuge.

A useful known process that can be used, in addition to the improvements described hereinafter, for removing undesirable materials comprises a high temperature vacuum steam distillation process, and involves deaerating the polyol polyester to a level of less than about 0.10% by volume of dissolved oxygen and heating the deaerated oil to a temperature between about 390° F. (200° C.) and about 480° F. (250° C.) and then stripping with a stripping medium in the amount of about 0.2% to about 20% by weight of the oil at an absolute pressure of less than about 15 mm Hg for a time of between about 5 seconds and about 15 minutes. This vacuum stripping at very high temperatures for short residence times minimizes the content of undesirable materials. It is desirable to either maintain the temperature below about 450° F. (230° C.), preferably less than about 350° F. (about 180° C.), in a batch deodorizer, or admix the polyol polyester with a fatty acid triglyceride to protect the polyol polyester from excessive thermal degradation.

The Improvements

The very low levels of color/odor/flavor materials, precursors, and/or oxidation products most preferred for use herein can be achieved by 1) treatment of the polyol polyester with the specific silica gel of this invention during or following the refining and finishing steps, 2) heat treating the polyesters to reduce the peroxide content, 3) removing the undesirable volatile materials, or 4) combinations of (1), (2), or (3).

The silica gel of this invention has the following properties: (a) a particle size of ranging from about 10 to about 30, preferably from about 20 to about 25 microns; (b) average pore diameter of from about 50 to about 70 microns; (c) surface area of from about 720 to about 800, preferably from about 770 to about 800 m$^2$/gm; (d) pore volume of from about 0.9 to about 1.9, preferably from about 1.2 to about 1.4 cm$^3$/gm; (e) a pH of from about 5 to about 8, preferably from about 6 to about 7.5, measured at a level of about 5% in water; and (f) total volatiles of less than about 20%, preferably from about 6.5% to about 10.5%, and more preferably from about 8% to about 10.5%. The silica gel is added to the product at levels of from about 0.25% to about 5%, preferably from about 1% to about 2%.

Neutral silica gels (i.e., those having a pH of from about 5 to about 8) are extremely effective as compared to other known materials. Applicants have discovered that the treatment of polyol polyesters with these neutral silicas can reduce oxidation compared to acid bleaching clays or silica gels. One way acidic clays bleach is by breaking down (oxidizing) the double bonds within the molecule, thus chemically altering the polyol polyester by destroying the color-producing conjugated system, and forming new, more volatile materials which are less stable. The neutral silica gel of this invention, on the other hand, can remove color bodies by absorbing impurities into the interior of the silica, without altering the structure of the polyol polyester or making the molecule unstable. Reduction of oxidation is particularly critical to polyol polyesters which, unlike triglycerides, do not contain natural stabilizers. Without natural stabilizers, even a small amount of oxidation can be detrimental to the stability of the molecule.

Neutral silica gels also reduce hydrolysis that can occur during refining and production of the polyol polyesters compared to acidic bleaching clays or silicas. This is critical to the purity of the final product. Hydrolysis can deesterify the fatty acid groups attached to the polyol backbone, causing the formation of free fatty acids. These free fatty acids then form soaps and adverse color effects.

Moreover, the particular total volatiles content of the silica gels of the present invention also helps reduce hydrolysis of the polyol polyester treated with these silicas. "Total volatiles" is defined herein as the loss in weight after heating a polyol polyester sample at 1750° F. for one hour. This loss in weight is considered to be free moisture expelled at 1750° F., but can also include minute amounts of volatile sulfates and ammonium compounds if these are present.

The silica of this invention is also important in preventing or inhibiting the formation of undesirable dimer esters in the polyol polyester. The amount of dimer ester that forms in polyol polyesters treated with acidic bleaching clays or silica gels is greater and more variable compared to polyesters treated with the neutral silicas of this invention. It is believed that neutral silica gels minimize condensation of hydroxy methyl esters, thereby reducing the formation of dimer esters. Since dimer esters lead to unacceptably high levels of toxic methanol in the final product, it is critical to control the formation of these dimers.

The use of the silica gel inevitably introduces oxygen, from entrapped air, into the polyester. It has been discovered that the oxygen can be consumed and the subsequently formed peroxide groups can be decomposed by raising the temperature to at least about 200° F. (about 90° C.), preferably at least about 380° F. (about 190° C.), but less than about 425° F. (about 220° C.), preferably less than about 400° F. (about 205° C.), and holding the product at the elevated temperature for a period of time sufficient to reduce the peroxygen content and/or reduce the content of colored materials present, e.g., from about 1 to about 150 minutes, preferably from about 1 to about 20 minutes, and most preferably from about 5 to about 10 minutes. (The level of oxygen in the polyol polyester is believed to be from about 0.001 to about 0.16 volumes of oxygen per volume of polyol polyester assuming similar values to those reported for triglycerides.) This can be accomplished separately, or in combination with a steam deodorization step, as described hereinbefore. When this heat treatment step is used, it is possible to use a wider range of silica gels in place of the preferred silica gel and achieve acceptable results. The best results, however, are achieved with the preferred silica gel.

The volatile materials created by heating first with oxygen and then in the absence of oxygen are alkanes, alcohols, esters, aldehydes, ketones, fatty acids, aromatics, and/or lactoses having molecular weights of less than about 300. In the preferred processes set forth herein, the amount of said volatile materials that needs to be removed is quite low, typically less than about 200 ppm, and, for the best processes, less than about 100 ppm. Despite the low level of such volatile materials, removal is important to the stability of the polyol fatty acid polyesters.

The removal of the volatile materials resulting from the heat treatment are preferably removed by steam deodorization. However, it is also possible to remove the volatile materials by any of the other known removal techniques including: (a) solvent extraction; (b) straight distillation under reduced pressure; (c) extraction with other gases to reduce the partial vapor pressure; (d) absorption on materials like silica gels, alumina, charcoal, molecular sieves, porous polymers, etc.; and (e) combinations of techniques. Steam deodorization, however, can provide the heat and is a relatively safe, inexpensive procedure that is commonly applied to fatty materials.

Any steam deodorization steps prior to the silica gel bleaching step and/or after the heat treatment step can be accomplished in the presence of a conventional triglyceride in ratios of higher polyol polyester to triglyceride of from about 1:10 to about 10:1, preferably from about 1:5 to about 5:1, more preferably from about 1:3 to about 3:1. This "codeodorization" minimizes thermal degradation of said polyester. The operating conditions for codeodorization are from about 300° F. (about 150° C.) to about 600° F. (about 315° C.), preferably from about 350°-525° F. (about 175°-275° C.); about 0.1-20 mm Hg (preferably about 1-10 mm Hg) vacuum; and steam to product ratio of about 0.001-0.30 (preferably 0.005-0.10). As compared to deodorization of the polyol polyester by itself, codeodorization permits the use of higher temperatures, e.g., from about 300° F. (150° C.) to about 600° F. (315° C.), preferably from about 350° F. (175° C.) to about 525° F. (275° C.), and/or longer times without excessive degradation and can be desirable if equipment limitations are present. The triglyceride is usefully any common triglyceride, e.g., those derived from cottonseed, peanut, safflower, sunflower, coconut, rapeseed, canola, palm, palm kernel, and/or soybean oils.

Combinations of one or more of these steps reduce the quantity of undesired materials to a very low level.

When the initial reactants have been properly cleaned up and the preceding clean-up steps have been applied properly, the color of the polyol polyester is less than about 1.5, preferably less than about 1.2 Lovibond Red, more preferably less than about 0.8 Lovibond Red, and the flavor grade of the polyol polyester is at least 7, preferably at least 8 panel score units (psu) as measured by a panel of experts using a grade system in which 10 is bland and 1 is severely oxidized. Such a finished polyol polyester has improved oxidative, flavor, and thermal stability during its subsequent uses. When combined with a typical triglyceride, containing natural antioxidants (e.g., tocopherols), in ratios of polyol polyester to triglyceride of from about 1:10 to about 10:1, preferably at ratios of from about 1:3 to about 3:1, more preferably at ratios of from about 1:3 to about 1:1, the stability is further surprisingly enhanced. Apparently, the reactive materials are reduced to a level where the natural antioxidants can provide improved long term stability. A useful composition comprises a naturally occurring triglyceride and from about 10% to about 75% of said finished polyol polyester.

Especially preferred polyol polyesters are those of sucrose which have been esterified to a level of more than about 65%, preferably from about 70% to about 90% octaester for "solid" shortenings. Such sucrose polyesters have superior thermal stability, especially when they contain only the low levels of color/odor materials and/or other oxidation products.

All percentages, parts and ratios herein are by weight unless otherwise specified.

EXAMPLE I

Methyl esters of a fully hydrogenated (Iodine Value about 1) soy oil (about 90.7 kg), about 20 kg of potassium hydroxide pellets, and about 136 kg of methanol are mixed in a stainless steel batch reactor. This mixture is then heated to about 145° F. (63° C.) with agitation for about 1 to 3 hours at atmospheric pressure. During this time, a portion of the methyl esters are saponified to form soap.

An additional about 591.9 kg of methyl esters of a partially hydrogenated soy oil with an I.V. of about 85, is then added to the soap mixture. The methyl esters are prepared by distillation under vacuum without fractionation. Granular sucrose (about 136.1 kg) is added to the soap/ester mixture to give an about 5:1 molar ratio of ester to sucrose. Granular potassium carbonate is then added to the mixture (~0.5% of the reaction mix) to catalyze the transesterification. This mixture is agitated and slowly heated at atmospheric pressure until the temperature reaches about 225° F. (107° C.). This is to remove the methanol. A vacuum is then pulled and the mixture agitated for up to about 4 hours to form the mono-, di-, and triesters. Small quantities of tetra- and pentaesters are also formed during this stage. Additional methyl ester (about 945.7 kg) is added to bring and maintain the molar ratio of the esters to sucrose to about 12:1. Additional potassium carbonate is then added to the mixture (~0.5% of the initial reaction mix). When the reaction conditions stabilize at about 275° F. (135° C.), a nitrogen sparge is used to improve agitation and promote methanol stripping. This second reaction stage lasts approximately 4 to 16 hours.

The reaction mixture is then cooled under nitrogen to between about 149° F. (65° C.) and about 185° F. (85° C.). The crude reaction mixture is agitated with between about 0.25% and about 6% water. The hydrated crude reaction mixture is passed through a centrifuge to separate a heavy and a light phase. The heavy phase which contains the soaps, excess sugars, and potassium carbonate is discarded.

The light phase which contains methyl esters and the sucrose polyester (SPE) is then dried to remove moisture at from about 160° F. (71° C.) to about 200° F. (93° C.) under about 70 mm Hg or less vacuum for about 30 to 60 minutes. Filtrol ™ 105, an absorbing clay, (about 0.5-3%) is added and the mix is agitated at about 167° F. (75° C.) to about 200° F. (93° C.). The slurry is separated by filtration or other means until there is less than 0.1% fines. The liquid is then passed through a 1 micron filter.

The refined and bleached reaction mix is then passed through a stainless steel wiped-film evaporator or other suitable equipment to distill off the bulk of the methyl esters. The distillation takes place at about 392° F. (200° C.) to about 455° F. (235° C.) under approximately 3 mm Hg of vacuum.

The SPE is then deodorized by passing downward through a stainless steel packed column deodorizer or other suitable device at from about 392° F. (200° C.) to about 482° F. (250° C.) under a vacuum of about 5 mm Hg or less. The lower than normal processing temperatures herein minimize formation of undesirable materials.

Steam is introduced to the bottom of the column and passes counter-currently to the sucrose polyester. Feed rates and temperature are adjusted until the methyl ester content of the SPE is below 1000 ppm. The mixture is then cooled to between about 130° F. (54.5° C.) and about 185° F. (85° C.) and passed through an about 1 micron filter.

SPE from the preceding reaction is bleached in 3 separate batches using between about 0.5% and 5.0 wt % silica gel at about 125°-350° F. (52°-177° C.) for from about 0.5 to 4.0 hours. The silica gel used in this example has a particle size of about 19 microns, an average pore diameter of about 54 Angstroms, surface area of about 770 m$^2$/gm, pore volume of about 1.0 cc/gm, a pH measured at about 8 measured in water at a concentration of about 5%, and total volatiles of about 8.9%. Even better performance is achieved using a silica gel with a particle size that ranges from about 20 to about 25 microns, a surface area of from about 770 to about 800 m$^2$/gm, pore volume of from about 1.2 to about 1.4 cc/gm, and pH of from about 6 to about 7.5 measured in water at about 5% concentration. Silica gel is added directly to the SPE in lined carbon steel drums with a nitrogen blanket and agitated. The slurry is separated by filtration until no fines are observed and then cooled. Color of the SPE is reduced from about 1.5 Lovibond Red and about 6.5 Lovibond Yellow to about 0.9 Lovibond Red and about 3.4 Lovibond Yellow.

The bleached and filtered SPE is then mixed with triglyceride in the presence of air in drums in a ratio of about 50:50 and deodorized in 5 separate batches. In each deodorizer batch, a total of about 154.2 kg of the mixture is transferred into the pot, nitrogen sparge is introduced and agitation started. Steam is generated by introduction of distilled water into the pot when temperature reaches about 250° F. (about 120° C.) during heatup. Deodorization is conducted at a temperature of about 400° F. (about 205° C.) for from about 2 hours to about 4 hours at about 3 mm Hg of vacuum. The mixture is then cooled and stored in clean drums. Color of the mixture is reduced from about 0.9 Lovibond Red and about 4.6 Lovibond Yellow to about 0.6 Lovibond Red and about 3 Lovibond Yellow during deodorization.

Increased oxidative stability in the presence of air is a substantial quality benefit because it equates with increased flavor stability. Good fresh flavor and flavor stability are key consumer expectations which strongly influence consumer satisfaction for an edible product. Poor oxidative stability results in generation of off flavors and odors during routine exposure to air encountered with product use and storage.

Oxidative stability of the SPE and the triglyceride/SPE mixture is also dramatically increased when prepared as described in Example 1. There are believed to be three primary contributing steps, each individually increasing stability, and together providing the most stable combination. The three steps are: (1) silica gel bleaching; (2) heat treatments either prior to continuous deodorization, or during batch deodorization (optionally codeodorizing with triglycerides); and (3) blending with triglyceride which contains natural antioxidants.

The silica gel which effectively reduces color, also removes undesirable materials resulting in increased oxidative stability of the polyol polyester. It is believed that heat treatment first forms peroxygen compounds from air absorbed during bleaching with the silica gel or by mixing with air and/or mixing with triglyceride in the presence of air, and then decomposes those peroxygen compounds into volatile oxidation products, such as hexanal, while excluding air, which oxidation products are subsequently removed by, e.g., steam deodorization. With the improved stability that results from the two preceding processes, blending with triglyceride containing natural antioxidants at a level of at least about 25%, preferably at least about 50%, triglyceride results in substantial oxidation stability improvement because there is now a sufficient level of natural antioxidants present in the triglyceride to also protect the polyol-polyester/triglyceride mixture.

Oxidative stability is measured using a modified Active Oxygen Method (AOM) which measures an increase in peroxide value (AOCS Method Cd 8-53) over time while sparging air through the sample at about 208° F. (about 98° C.). The AOM is a standard method used in the fats and oils industry to measure oxidative stability of triglyceride. (AOCS Method Cd 12-57) This method has been modified for ease of application in the time frame of 0-5 hr. where oxidation impact on flavor is especially important. The method used to measure stability is described as follows:

Charge 300 gm of sample into the glass flask, and begin purging the sample with nitrogen.

Heat to about 208° F. (about 98° C.) using a heating mantle connected to a thermo watch to control temperature.

Switch from nitrogen to air at about 8.57 cc/min./ml of sample and collect a baseline sample for time zero reference and analyze for ppm peroxide.

Collect samples every 20 to 40 min. and analyze for ppm peroxide.

The first table is included to show the effect of silica gel bleaching on stability of SPE.

TABLE 1

| Effect of Silica Gel Bleaching on SPE Stability | | |
|---|---|---|
| | Peroxide Value (ppm) | |
| Time (Min.) | Unbleached SPE | Bleached SPE |
| 0 | 11.8 | 5.5 |
| 20 | 22.8 | 10.0 |
| 40 | 36.1 | 13.2 |
| 60 | 40.3 | 14.6 |
| 90 | 47.2 | 19.0 |
| 120 | 43.9 | 23.2 |

As can be seen from Table 1, peroxide value is substantially greater in the sample of SPE which was not treated with silica gel. At 120 min. the untreated sample contains 89% more peroxide than the treated sample.

Heat treatment was accomplished in the batch deodorizer at the high temperature and long residence time during deodorization of the mixture of SPE and triglyceride. Without the triglyceride being present, a temperature of from about 275° F. (about 135° C.) to about 350° F. (about 175° C.) is used. In the deodorizer any absorbed oxygen forms peroxides which are then decomposed into volatile oxidation products that are subsequently removed by steam deodorization. This heat treatment step prevents high levels of peroxides from passing through deodorization and into storage and finished product application where they eventually decompose and impart off-flavors into the product. In a continuous deodorization process where residence time is comparatively short, a separate heat treatment step is used just prior to deodorization to increase formation and/or breakdown of the peroxides.

The second table illustrates the unexpected stability benefit gained from blending with triglyceride and using the natural antioxidants present in the triglyceride to provide the most stable mixture. SPE contains little or no natural antioxidants because of their removal in multiple processing steps in making methyl esters from triglyceride and the production of SPE.

TABLE 2

Effect of Blending SPE with Triglyceride on Stability

| | Peroxide Value (ppm) | | |
|---|---|---|---|
| Time (Min.) | Triglyceride | Bleached, Heat Treated and Deodorized SPE | Mixture |
| 0 | 6.7 | 5.5 | 5.9 |
| 20 | 7.3 | 10.0 | 5.6 |
| 40 | 8.2 | 13.2 | 6.0 |
| 60 | 9.6 | 14.6 | 7.9 |
| 90 | 10.5 | 19.0 | 7.4 |
| 120 | 11.7 | 23.2 | 12.4 |

SPE bleached with silica gel and heat treated is clearly less stable than either the triglyceride or the SPE/triglyceride blend. Careful inspection of the data will reveal that blend stability is very near that of the triglyceride itself, not merely a blend of their respective stabilities. The peroxide value for a blend of a triglyceride and SPE is often actually higher than the arithmetic average of the individual components. With the exception of the last data point at 120 min., the blend is actually more stable than the triglyceride although this may not be significant because of normal variability in the modified AOM and peroxide value methods.

When the SPE is sufficiently treated to improve stability prior to blending, the level of natural antioxidants in the triglyceride is able to protect the entire mixture. Without thorough treatment to improve SPE stability prior to blending, the level of natural antioxidants in the triglyceride afford little benefit toward protecting the SPE from oxidation.

Since this particular modified AOM stability method accelerates the effects of exposure to air by providing intimate contact at a temperature relatively high compared to normal storage and handling conditions prior to use in finished product applications, these stability benefits are greatly magnified during normal storage and handling procedures which are at much less severe conditions. Benefits are also realized by separate deodorization of SPE and triglyceride followed by immediate blending under nitrogen to avoid contact with air and subsequent generation of peroxides.

Blending SPE with undeodorized oil, which contains greater levels of natural antioxidants than deodorized oil, provides even greater stability benefits during extended storage prior to deodorization. This is especially advantageous in manufacturing facilities where extended storage and large scale handling of SPE without some incidental air contact are not possible.

EXAMPLE 2

This example demonstrates the stabilizing effects of post bleaching and heat treatment on SPE followed by continuous deodorization without triglyceride present.

The SPE is prepared using about 54 parts of hardened (I.V. ~1) and about 46 parts of partially hardened soybean methyl esters (I.V. ~85) in a manner similar to that in Example 1 prior to the addition of silica gel.

About 1200 gm of SPE at about 140° F. (60° C.) is added to a glass 2 liter reaction flask which has been flushed with nitrogen to remove air. A vacuum of approximately 5 mm Hg is provided to deaerate the SPE while heating to about 200° F. (93° C.). When bleaching temperature is reached the vacuum is broken with nitrogen and about 36 gm of silica gel is added and agitation is started. The SPE is sparged with nitrogen for about 0.5 min. and vacuum is reapplied for about 10 min. to deaerate the silica gel. The vacuum is broken with nitrogen and agitation is continued for approximately 1 hour. The SPE is filtered with a Buchner funnel using Whatman 40 filter paper.

The silica gel used in this example has a particle size of about 20 microns, an average pore diameter of about 65 Angstroms, surface area of about 770 $m^2$/gm, pore volume of about 1.4 cc/gm, a pH measured at a concentration of about 5% in water, and total volatiles of about 10.3%.

Use of other types of silica gel will not result in the same degree of color improvement. A total of 10 other different types of silica gel were tested with SPE and none reduce color levels to the same extent. The types of silica gel evaluated have pore volumes between about 0.34–1.9 cc/gm, surface area between about 320–800 sq. m/gm, total volatiles between about 5.7–20 wt %, pH between about 3–8, an average pore diameter between about 20 and about 200 Angstroms, and average particle size between about 10–30 microns.

The silica gels that were evaluated with the SPE of Example 1 had the following characteristics.

| Average Pore Diameter (Angstroms) | % Color Reduction (Lovibond Red) |
|---|---|
| 20.4 | 36 |
| 65.0 | 63 |
| 68.4 | 63 |
| 122 | 45 |
| 202 | 27 |

As can be seen from the above, Pore Diameters that are larger than about 70 Angstroms and smaller than about 50 Angstroms do not provide the optimum color removal that, in combination with the other process steps, provides superior polyol fatty acid polyester.

Only silica gel with a combination of the hereinbefore stated requisite properties is able to achieve a greater than an 80% color reduction on SPE made by the described reaction process. The silica gel of choice is also best suited to remove undesirable color materials generated in the reaction by thermal degradation caused by excessive reaction temperature. The most preferred silica gel is the only type capable of removing about 44% of color generated by thermal degradation in a single treatment. This makes it the overall best choice for consistently producing best possible color material by removing the greatest amount of undesirable color materials.

A portion of the bleached and filtered SPE is then heat treated by elevating the temperature to about 414° F. (212° C.) for a period of about 18 min. while excluding the presence of air.

Table 3 illustrates the of effects of silica gel treatment and heat treatment on SPE using the modified AOM method. The unbleached, bleached, and bleached and heat treated samples are all deodorized as a final step. Data is reported as the time it takes to reach a specified peroxide value. Initial peroxide values of unbleached, bleached, and bleached and heat treated SPE are about 55, 35, and 20 ppm, respectively. Both bleached, and bleached and heat treated, were continuously deodorized in a small glass laboratory steam deodorizer after treatment.

TABLE 3

Effect of Silica Gel Bleaching and Heat Treatment on Oxidative Stability

| Specified PV (ppm) | Time Required to Reach Specified Peroxide Value (Min.) | | |
|---|---|---|---|
| | Unbleached | Bleached | Bleached and Heat Treated |
| 100 | 22 | 70 | 115 |
| 200 | 40 | 92 | 140 |
| 400 | 58 | 120 | 162 |
| 600 | 80 | 146 | 177 |

In order to reach a peroxide value of 100 ppm, only about 22 min. is required for an unbleached SPE, while bleached and heat treated SPE requires about 115 min. This example shows that with silica gel bleaching and bleaching with heat treatment, oxidative stability of the SPE is substantially improved over untreated SPE. The bleached and heat treated SPE is over 4 times as oxidatively stable up to a 100 ppm peroxide value. Deodorization is required after bleaching and heat treatment to achieve good flavor by removing oxidation products which are generated.

EXAMPLE 3

This example demonstrates the oxidative and hydrolytic improvements of polyol polyesters treated with the specific silica gel of this invention relative to acid activated bleaching clay. A sucrose polyester is prepared using about 54 parts of hardened (I.V. about 1) and about 46 parts of partially hardened (I.V. about 85) soybean methyl esters in a manner consistent to that of Example 1 prior to crude refining.

Two aliquots of 1000 g. each are placed in glass flasks and flushed with nitrogen while heating to 160° F. (71° C.). To each flask, 62.5 g. of heated 160° F. (71° C.) deionized water is added. The mixtures are agitated for 10 minutes and then separated using a large laboratory centrifuge. Both samples are then dried by heating to 160° F. (71° C.) under vacuum of about 5 mmHg for approximately 30 minutes. After drying, each sample has a peroxide content of about 50 ppm and free fatty acid content of about 100 ppm. The vacuum is broken with nitrogen and 25.7 g. of silica gel is added to Sample 1 and 12.8 grams of bleaching clay is added to Sample 2. The silica gel has a particle size of about 20 microns, an average pore diameter of about 65 Angstoms, surface area of about 773 m²/g, pore volume of about 1.36 cc/g, total volatiles of 10.3 and pH of about 7.3 measured at a concentration of 5% in water. The clay has a particle size of about 43 microns, moisture content of about 16.2% and pH of about 3.5 measured at a concentration of 25% in water.

Both Samples are then agitated and deaerated under vacuum of about 5 mmhg while heating. When a bleaching temperature of 200° F. (93° C.) is reached, the vacuum is broken with nitrogen. Bleaching is continued for about 1 hour, and then the Samples are filtered with a Buchner funnel using Whatman 40 filter paper.

Next, the samples are thermally evaporated to reduce the amount of excess methyl ester from about 36% to below 1000 ppm. This is achieved by heating the samples to a temperature of about 410° F. (210° C.) under about 1 mmHg of vacuum in a laboratory evaporator. After evaporation, both Samples have a color of 1.0 Lovibond Red units, but Sample 1 has a peroxide content of about 11 ppm and free fatty acid content of 100 ppm, compared to a peroxide content of about 136 ppm and a free fatty acids content of 200 ppm for Sample 2. This illustrates that oxidation and hydrolysis are significantly reduced in Sample 1 compared to Example 2. This reduction is further emphasized by examination of the distillates from these samples. The Sample 1 distillate had a peroxide content of 12 ppm, free fatty acids content of 400 ppm, and a carbonyl content of 120 ppm, compared to a peroxide content of about 21 ppm, a free fatty acid content of about 1,900 ppm and a carbonyl content of about 590 ppm for Sample 2.

EXAMPLE 4

Sucrose polyester is prepared in the same manner as Example 1 prior to silica gel treatment with the exception that about 78 parts hardened soybean methyl ester with an I.V. of about 1, and about 22 parts partially hardened soybean methyl esters with an I.V. of about 85 are used as the methyl esters for the reaction.

In this example the SPE is heat treated and codeodorized in about a 40:60 blend SPE/triglyceride without prior silica gel treatment of the SPE. SPE is first mixed with triglyceride in clean drums without excluding air which provides contact with oxygen. The mixture is then deodorized/heat treated in four separate batches consisting of about 161 kg per batch. This codeodorization is conducted in the same manner as codeodorization described in Example 1 at about 400° F. (about 204° C.) for a period of from about 2 hours to about 4 hours. After deodorization the mixture is then cooled and stored in clean drums.

A mixture is then made of the SPE/triglyceride blend produced in Example 1 with the SPE/triglyceride blend produced in Example 3 in a ratio of about 60:40. Blending of these two mixtures is accomplished by melting material stored in drums and pumping into a stainless steel tank with agitation. Additional typical minor ingredients used to prepare shortening are added to this 60:40 mixture. The resulting final mixture produces a solid shortening with substantially improved color and oxidative stability.

EXAMPLE 5

Deodorization with steam is used in initial manufacture of SPE, and again after exposure to oxygen and extended storage has degraded flavor, to improve flavor by removing oxidation by-products. However, darkening will occur by thermal degradation if temperatures normally used in triglyceride processing are applied. Adding triglyceride to the SPE and then deodorizing the mixture, termed "codeodorization", allows this to be successfully accomplished at higher temperatures with lower steam usage than with SPE alone.

Impact of deodorization temperatures on flavor and color of SPE and SPE/triglyceride mixtures is investigated using a small one-pound batch deodorizer in the laboratory. Temperature effects are shown between about 300° F. (150° C.) and about 450° F. (230° C.) for about 2-3 hours at a pressure of about 3 mm Hg. Distilled water is injected into the deodorizer beginning at about 250° F. (120° C.) to produce steam.

The SPE is prepared in a manner similar to that of Example 2, using hardened and partially hardened soybean methyl esters, prior to the addition of silica gel. The blend ratio used in the SPE/triglyceride mixture is 1:2. The SPE has undergone steam deodorization to remove residual methyl esters in its manufacture: the triglyceride has been refined and bleached without deodorization.

Table 5 presents the results of steam deodorization on color of SPE and the 1:2 SPE/triglyceride blend at various times and temperatures.

TABLE 5

Effect of Time and Deodorization Temperature on Color

| Material | Temp. (F.°) | Time (Hr.) | Flavor | McCloskey Color Red | McCloskey Color Yellow |
|---|---|---|---|---|---|
| SPE | ambient | 0 | 6.5* | 2.3 | 12.8 |
| Blend | ambient | 0 | — | 2.2 | >40 |
| SPE | 300 | 3 | 7.6 | 2.9 | 16 |
| Blend | 300 | 3 | 5.0 | 1.5 | 34 |
| SPE | 350 | 3 | 7.5 | 3.0 | 16 |
| Blend | 350 | 3 | 8.1 | 1.1 | 14 |
| SPE | 400 | 3 | 7.8 | 7.8 | 40 |
| Blend | 400 | 3 | 7.7 | 0.6 | 5 |
| SPE | 450 | 2 | 7.7 | 21.5 | 34 |
| Blend | 450 | 2 | 7.0 | 3.1 | 14 |

*Flavor of the SPE is measured in an SPE/triglyceride blend of 1:2 to facilitate flavor grading. The flavor of the triglyceride used to flavor the blend is 7.7. Flavor data is not available for the initial blend prior to deodorization.

The red color of the SPE without triglyceride increases with increasing temperature. At about 450° F. (230° C.) there is a dramatic increase in red color even at a residence time of only about two hours. Yellow color also increases with temperature, but not as rapidly. In the blend, red color initially decreases with time and then increases at about 450° F. (230° C.). After two hours at about 450° F. (230° C.), the red color of the SPE has increased about six times compared with that of the blend, and yellow color has increased about one and a half times.

If the SPE deodorized at about 450° F. (230° C.) for about two hours with a final red color of about 21.5 is mixed in an approximately 1:2 ratio with a typical deodorized triglyceride having a color of about 0.5, the final blend color is about 6.8 Red. A final blend color of about 3.1 indicates that the color effect is not just dilution of SPE color with triglyceride, but that addition of triglyceride prevents thermal degradation of the SPE and corresponding color increase. Measurement of percent polymer at about 450° F. (230° C.) for two hours shows an increase from <0.1% to 0.8% with the SPE, and no increase from <0.1% in the blend. This provides further evidence that the triglyceride protects SPE from thermal degradation.

Flavor of all samples after deodorization increased to acceptable levels of greater than or equal to about 7.0 with the exception of the blend at about 300° F. (150° C.) for three hours. This is because at the low temperature not all of the components from the undeodorized triglyceride were removed.

In continuous deodorization it is believed that higher temperatures could be achieved for both SPE and the SPE/triglyceride blend because of the shorter residence times involved with continuous deodorization operation. However, the blending of triglycerides would still enable operation of the continuous deodorizer at higher temperatures than with SPE alone. Higher temperature deodorizer operation enables lower steam usage to remove the same levels of volatiles, and allows deodorization of SPE to be accomplished more readily on existing oil deodorizers without significant modification to accommodate lower temperatures.

What is claimed is;

1. A process for removing undesirable reaction products from higher polyol fatty acid polyesters and for preventing or inhibiting oxidation, hydrolysis and the formation of dimer methyl esters during synthesis of the polyol fatty acid polyester, which process comprises treating the crude polyesters with a silica gel having:
   (a) particles ranging in size from about 10 to about 30 microns;
   (b) an average pore diameter of from about 50 to about 70 Angstoms;
   (c) surface area of from about 720 to about 800 square meters per gram;
   (d) pore volume of from about 0.9 to about 1.9 cc/gm;
   (e) pH of from about 5 to about 8 when measured at a concentration of about 5% in water; and
   (f) total volatiles of less than 20%;
such that the polyol fatty acid polyester contains minimal peroxides, free fatty acids and dimer methyl esters after treatment with the silica gel.

2. The process of claim 1 wherein the silica gel has: (a) a particle size that ranges from about 20 to about 25 microns; (b) surface area of from about 770 to about 800 $m^2$/gm; (c) pore volume of from about 1.2 to about 1.4 cc/gm; (d) pH of from about 6 to about 7.5; and (e) total volatiles of from about 6.5% to about 10.5%.

3. The process of claim 2 wherein the silica gel has total volatiles of from about 8% to about 10.5%.

4. The process of claim 1 additionally comprising the step of removing undesirable volatile materials from the polyol fatty acid polyester after treatment of the polyol polyester with the silica gel.

5. The process of claim 4 wherein the removal of undesirable volatile materials is accomplished by solvent extraction; straight distillation under reduced pressure; extraction with other gases to reduce partial vapor pressure; absorption on the materials selected from the group consisting of gels, alumina, charcoal, molecular sieves, and porous polymers; steam deodorization; or combinations thereof.

6. The process of claim 5 wherein the removal of undesirable volatile material is accomplished by steam deodorization.

7. The process of claim 6 wherein the peroxide value of the polyol fatty acid polyester 120 minutes after treatment with the silica gel is less than about 400 ppm.

8. The process of claim 7 wherein the polyol fatty acid polyester contains less than about 100 ppm of free fatty acids after treatment with the silica gel.

9. The process of claim 8 wherein the carbonyl number of the fatty acid methyl esters which are separated from the polyol fatty acid polyesters during the process is less than about 200 ppm.

10. The product prepared according to the process of claim 9.

11. The product prepared by the process of claim 4.

12. A polyol fatty acid polyester product prepared according to a process for removing for removing undesirable reaction products from higher polyol fatty acid polyesters and for preventing or inhibiting oxidation, hydrolysis and the formation of esters during synthesis of the polyol fatty acid polyester, which process comprises treating the crude polyesters with a silica gel having:

(a) particles ranging in size from about 10 to about 30 microns;

(b) an average pore diameter of from about 50 to about 70 Angstroms;

(c) surface area of from about 720 to about 800 square meters power gram;

(d) pore volume of from about 0.9 to about 1.9 cc/gm;

(e) pH of from about 5 to about 8 when measured at a concentration of about 5% in water; and (f) total volatiles of less than 20%;

such that the polyol fatty acid polyester contains minimal peroxides, free fatty acids and dimer methyl esters after treatment with the silica gel.

13. A composition comprising from about 25% to about 90% of a triglyceride fat or oil containing natural oxidants and from about 10% to about 75% of the polyol fatty acid polyester product of claim 12.

* * * * *